(12) United States Patent
Chung et al.

(10) Patent No.: US 8,188,049 B2
(45) Date of Patent: May 29, 2012

(54) PEPTIDES HAVING ACTIVITIES OF EPIDERMAL GROWTH FACTOR AND ITS USES

(75) Inventors: Yong-Ji Chung, Yongin-sio (KR); Young Deug Kim, Siheung-si (KR); Eun Mi Kim, Jeollanam-do (KR); Jun Young Choi, Seoul (KR); Sang Su Song, Seoul (KR)

(73) Assignee: Caregen Co., Ltd., Gunpo-si, Gyeonggi-do (KR)

( * ) Notice: Subject to any disclaimer, the term of this patent is extended or adjusted under 35 U.S.C. 154(b) by 337 days.

(21) Appl. No.: 12/444,874

(22) PCT Filed: Oct. 8, 2007

(86) PCT No.: PCT/KR2007/004895
§ 371 (c)(1),
(2), (4) Date: Apr. 9, 2009

(87) PCT Pub. No.: WO2008/044846
PCT Pub. Date: Apr. 17, 2008

(65) Prior Publication Data
US 2010/0120696 A1 May 13, 2010

(30) Foreign Application Priority Data

Oct. 10, 2006 (KR) .................. 10-2006-0098368

(51) Int. Cl.
| | |
|---|---|
| *A61K 38/00* | (2006.01) |
| *A61K 38/04* | (2006.01) |
| *A61P 17/00* | (2006.01) |
| *A61P 17/14* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl. ...... 514/18.6; 514/20.7; 530/326; 530/327; 530/328

(58) Field of Classification Search ................. None
See application file for complete search history.

(56) References Cited

U.S. PATENT DOCUMENTS

| | | | |
|---|---|---|---|
| 4,179,337 A * | 12/1979 | Davis et al. ................ 435/181 |
| 5,169,933 A * | 12/1992 | Anderson et al. .......... 530/391.3 |
| 5,183,805 A | 2/1993 | Lee et al. |
| 5,677,276 A * | 10/1997 | Dickerson et al. ............. 514/9.4 |
| 6,051,429 A * | 4/2000 | Hawley-Nelson et al. ... 435/458 |
| 6,638,912 B2 | 10/2003 | Bhatnagar et al. |

FOREIGN PATENT DOCUMENTS

WO    WO 92/08804    5/1992

OTHER PUBLICATIONS

Kessler et al. Inhibition of Tumor Growth by RGD Peptide-Directed Delivery of Truncated Tissue Factor to the Tumor Vasculature. Clin Cancer Res. Sep. 1, 2005. vol. 11, No. 17, pp. 6317-6324.*
Heath et al., "A Synthetic Approach to Structure-function Relationships in the Murine Epidermal Growth Factor Molecule," Proc. Natl. Acad. Sci. U.S.A. 83:6367-6371, 1986.
Johns et al., "Identification of the Epitope for the Epidermal Growth Factor Receptor-specific Monoclonal Antibody 806 Reveals That It Preferentially Recognizes an Untethered Form of the Receptor," J. Biol. Chem. 279:30375-30384, 2004.
Komoriya et al., "Biologically Active Synthetic Fragments of Epidermal Growth Factor: Localization of a Major Receptor-binding Region," Proc. Natl. Acad. Sci. U.S.A. 81:1351-1355, 1984.
Li et al., "Identification and Characterization of a Novel Peptide Ligand of Epidermal Growth Factor Receptor for Targeted Delivery of Therapeutics," FASEB J. 19:1978-1985, 2005.
Nakamura et al., "Peptide Mimics of Epidermal Growth Factor (EGF) with Antagonistic Activity," J. Biotechnol. 116:211-219, 2005.
International Search Report from International Application No. PCT/KR2007/004895, dated Jan. 10, 2008.

* cited by examiner

*Primary Examiner* — Marcela M Cordero Garcia
(74) *Attorney, Agent, or Firm* — Clark & Elbing LLP

(57) ABSTRACT

The present invention relates to peptides comprising the amino acid sequence represented by the following formula 1 and having the activities of epidermal growth factor and their uses: Cys-Met-Tyr-Ile-Glu-Linker-Arg-Gly-Asp (1) The EGF-mimicking peptides of the present invention possess identical functions or activities to natural-occurring human EGF and are able to promote the generation of autocrine EGF in cells. In addition the peptides of the present invention are much higher stability and skin penetration potency than natural-occurring EGF. Therefore, the composition containing the peptide exhibits excellent treatment and prevention efficacies on diseases or conditions demanding EGF activities, and can be advantageously applied to pharmaceutical compositions, quasi-drugs and cosmetics.

10 Claims, 8 Drawing Sheets

PEPTIDES HAVING ACTIVITIES OF EPIDERMAL GROWTH FACTOR AND ITS USES

CROSS-REFERENCE TO RELATED APPLICATIONS

This application claims priority under 35 U.S.C. §371 from international application PCT/KR2007/004895, filed Oct. 8, 2007, which claims priority from Korean Patent Application 10-2006-0098368, filed Oct. 10, 2006.

BACKGROUND OF THE INVENTION

1. Field of the Invention

The present invention relates to peptides having the activities of epidermal growth factor and their uses.

2. Description of the Related Art

Human epidermal growth factor consisting of 53 amino acid residues was first isolated by Dr. Stanley Cohen from mouse submandibular gland, and was elucidated to accelerate eyelid opening in the precocious new born mice (Cohen, S. (1962) *J. Biol. Chem*, 237, 1555-1562). Dr. Stanly Cohen was awarded Novel medical prize in 1986 for EGF studies. EGF, a polypeptide containing 3 disulfide bonds (Savage, C. t., Jr. et al., (1973) *J. Biol. Chem*. 248, 7669-7672; Savage, C. R., Jr. et al., (1972) *J. Biol. Chem*. 247, 7612-7621), triggers a signal transduction cascade via EGF receptor to induce growth and division of mammalian cells, particularly epithelium and skin cells, thereby promoting growth of epithelial cells (Sporn, M. B. et al., (1985) *Nature (London)* 313, 745-747; Sporn M. B. et al., (1980) *N. Engl. J. Med.* 303, 878-880). Furthermore, EGF has been reported to play a pivotal role in molecular regulation of wound healing (Buckley, A. et al., (1985) *Proc. Natl. Acad. Sci.* USA. 82, 7340-7344).

EGF is present at high level in various body fluids such as saliva, urine, milk, tear and blood. Upon being wounded, EGF provided to injured sites through blood stream contributes to wound healing without scar. In addition, EGF together with FSH (follicle stimulation hormone) is involved in maturation of fertilized egg in the uterus and EGF is responsible for regeneration of the cornea that is liable to degeneration due to the absence of blood vessels. Moreover, EFG plays a very important role in skin regeneration through the following various actions: promoting proliferation of epithelia and endothelia cells; promoting proliferation of fibroblasts to synthesize collagen in dermis; promoting angiogenesis at wounded sites; inducing secretion of factors implicated in regeneration; and promoting biosynthesis of fibronectin to form networking of skin tissues.

Human body responds to the occurrence of wounds and supplies EGF to injured tissues for healing. However, where the supply of EFG is not sufficient in body, exogenous EGF should be provided to go back to normal and healthy states. In this regard, EGF is considered to have a large multitude of applications. For example, EGF may be applied to diabetic foot ulcer, burn, wound, cornea injury, laparotomy, cosmetic peeling and skin aging. Besides epithelial cell proliferative potencies, hEGF has been suggested to be useful in treatment of gastric ulcer by preventing secretion of gastric acid (Gregory, H., (1985) *J. Cell Sci. Suppl.* 3, 11-17).

hEGF in urine was purified and characterized in 1975 by Dr. Srarkey; thereafter much efforts have been made to prepare hEGF in much higher yield and amount (Starkey, R. H. et al., (1975) *Science* 189, 800; Cohen. S. et al., (1975) *Proc. Natl. Acad. Sci.* USA 72, 1317). Several laboratories have reported a successful cloning of the hEGF gene (Smith, J. et al., (1982) *Nucleic Acids Res.* 10, 4467-4482; Urdea, M. S. et al., (1983) *Proc. Natl. Acad. Sci.* USA 80, 7461-7465; Oka, T, et al., (1985) *Proc. Natl. Acad. Sci.* USA 82, 7212-7216). However, hEGF prepared by the genetic recombinant technologies has not yet been produced in a large amount and high activities useful in industry fields.

Most of polypeptide growth factors present in blood and tissues have in vivo half life as short as several minutes. Likely, EGF shows poor structural stability. In addition, since EGF is biologically unstable and physiochemically heterogeneous, it is likely to show reduced treatment efficacies. Its skin permeation is far poor.

Accordingly, there remain needs to develop novel substances having improved stability and skin permeation potency as well as possessing EGF inherent activities.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing peptides having actions identical to natural-occurring human epidermal growth factor as well as having more enhanced stability and skin penetration than natural-occurring EGF, the present inventors have prepared and screened a multitude of human EGF-derived peptides. As a result, we have finally developed peptides excellent characteristics described above.

Accordingly, it is one object of this invention to provide a peptide having the activity of epidermal growth factor (EGF).

It is another object of this invention to provide a composition for preventing or treating an epidermal growth factor-effective disorder or condition.

Other objects and advantages of the present invention will become apparent from the following detailed description together with the appended claims and drawings.

In one aspect of this invention, there is provided a peptide having the activity of epidermal growth factor (EGF), which comprises the amino acid sequence represented by the following formula 1:

Cys-Met-Tyr-Ile-Glu-Linker-Arg-Gly-Asp  (1)

In another aspect of this invention, there is provided a composition for preventing or treating an epidermal growth factor-effective disorder or condition, which comprises as an active ingredient the present peptide having the activity of epidermal growth factor (EGF).

For developing peptides having actions identical to natural-occurring human epidermal growth factor as well as having more enhanced stability and skin penetration than natural-occurring EGF, the present inventors have prepared and screened a multitude of human EGF-derived peptides. As a result, we have finally discovered peptides excellent characteristics described above.

The developmental strategies of the present inventors are as follows: First, the present peptides are designed to comprise two regions, a EGF-derived sequence (i.e., EGF active region) and a cell attachment region. The EGF active region is selected from natural-occurring EGF amino acid sequence. To enhance the EGF activities of the present peptides, the cell attachment region is selected from fibronectin, one of extracellular matrix proteins.

The EGF active region finally selected comprises the amino acid sequence, "Cys-Met-Tyr-Ile-Glu" (SEQ ID NO: 4) and the cell attachment region finally selected comprises the amino acid sequence, "Arg-Gly-Asp". Furthermore, the present inventors have found that the indirect linkage of two regions via linkers is preferable than direct linkage.

According to the development strategies, the EGF-mimicking peptides represented by the formula 1 are prepared.

The linker to interconnect the EGF active region and the cell attachment region comprises any linker available to one of skill in the art. Preferably, the linker comprises a plurality of amino acids. Details of peptide linkers are found in Huston, et al., *Methods in Enzymology*, 203:46-88 (1991), and Whitlow, et al., *Protein Eng.*, 6:989 (1993), teachings of which are incorporated herein by references. A suitable linker in the present invention comprises amino acids having uncharged side chains, preferably, Gly or Gly or Ser. Preferably, the linker is 2-18 amino acid residues in length. More preferably, the linker comprises 2-10 Gly residues. The linker composed of amino acid residues, in particular Gly residues, contributes to the stability of the present peptides.

Even though the peptides of this invention per se have higher stability than natural-occurring EGF, its modification enables to have much higher stability. Preferably, the peptides of this invention have at their N-terminal or C-terminal a protection group selected from the group consisting of acetyl group, fluorenyl methoxy carbonyl group, formyl group, palmitoyl group, myristyl group, stearyl group or polyethylene glycol (PEG). The protection groups are also responsible for the stability of the present peptides.

Alternatively, the C-terminal of the peptide represented by the formula 1 is modified to have amino groups, which enhances the peptide stability.

The term used herein "stability" refers to in vivo stability and storage stability (e.g., storage stability at room temperature) as well. The protection group described above protects the peptides from the attack of protease in vivo.

According to a preferred embodiment, the Asp residue positioned at the C-terminal of the peptide is additionally linked to an Ala or Gly residue (more preferably, Gly residue) as a protection group.

According to the most preferred embodiment, the peptide comprises the amino acid sequence represented by the following formula 2:

```
                                        (SEQ ID NO: 3)
   Cys-Met-Tyr-Ile-Glu-Gly(n)-Arg-Gly-Asp-Gly    (2)
``` wherein n is an integer of 2-8.

The amino acid sequence of the exemplary peptide is set forth in SEQ ID NO:1.

The peptide of the present invention comprises the amino acid sequence represented by the Formula 1. Preferably, the peptide consists essentially of the amino acid sequence represented by the Formula 1. Most Preferably, the peptide consists of the amino acid sequence represented by the Formula 1.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)).

The principle underlying the structure of the present peptides is the linkage of EGF-derived sequences and fibronectin-derived cell attachment sequences. Therefore, it would be obvious to those skilled in the art that the Formula 1 is described to indicate the peptides of this invention in more convenient manner and the modifications or variants of the Formula 1 falling within the spirit of the invention are encompassed in the scope of this invention. For instance, the peptide having opposing position of the EGF-derived sequence and fibronectin-derived cell attachment sequence, i.e., "Arg-Gly-Asp-linker-Cys-Met-Tyr-Ile-Glu" (SEQ ID NO: 5) falls within the scope of this invention. Furthermore, the peptides comprising additional amino acid residues (e.g., 1-2 amino acid residues) to the EGF-derived sequence and/or fibronectin-derived cell attachment sequence falls within the scope of this invention. For example, where the C-terminal of the cell attachment sequence Arg-Gly-Asp is modified to further contain a Ser residue, the peptide falls within the scope of this invention.

The present peptides possess activities of naturally occurring human EGF and show higher stability to physiochemical factors such as acid and alkali. The peptides of this invention having significant long-term storage stability can be advantageously applied to products requiring long-term storage such as drugs, quasi-drugs, cosmetics and tooth/mouth cleaning or caring products.

In another aspect of this invention, there is provided a composition for preventing or treating an epidermal growth factor-effective disorder or condition, which comprises as an active ingredient the present peptide having the activity of epidermal growth factor (EGF).

In still another aspect of this invention, there is provided a method for preventing or treating an epidermal growth factor-effective disorder or condition, which comprises administering to a subject a composition comprising the peptide of the present invention.

In a further aspect of this invention, there is provided a use of the peptide of the present invention for manufacturing a composition for preventing or treating an epidermal growth factor-effective disorder or condition.

Since the present composition comprises the peptide of this invention as active ingredients described above, the common descriptions between them are omitted in order to avoid undue redundancy leading to the complexity of this specification.

The peptide of this invention as active ingredients contained in the present composition has EGF activities and shows in vivo functions and efficacies identical or similar to natural-occurring EGF. The term used herein "EGF activities" refers to any and all activities of natural-occurring EGF known to one of skill in the art, for example, including promotion of cell proliferation and division. Since the peptide of this invention is prepared to mimic the actions of natural-occurring EGF, it can exert all in vivo activities of natural-occurring EGF.

Because the peptide of this invention exhibits functions and actions identical or similar to natural-occurring EGF and shows higher biological activities than natural-occurring EGF, it can be advantageously applied for preventing or treating EGF-effective disorders or conditions. The term used herein "EGF-effective disorders or conditions" refers to disorders or conditions able to be prevented or treated by natural-occurring EGF.

According to a preferred embodiment, the composition of the present invention has efficacies or activities on promotion of cell growth and division, activities of epithelial cells, angiogenesis, neuron regeneration, wound healing, thrombosis treatment, atherosclerosis treatment, biosynthesis of collagen, elastin, laminin and hyaluronic acid, treatment of periodontal diseases or improvement of skin conditions.

Where the present composition is applied to treatment of periodontal diseases, it may be formulated to provide toothpastes or compositions for tooth and mouth cleaning or caring. The term "composition for treating periodontal diseases" may be interchangeably used herein with other terms, "composition for tooth and mouth caring" and "composition for tooth and mouth cleaning". The peptide of this invention promotes biological activities of epithelial cells present in gum tissues and heals gum wound to regenerate damaged gum tissues, thereby treating or preventing periodontal diseases.

More preferably, the composition of the present invention has efficacies on the improvement of skin conditions. In particular, the peptides used as active ingredients in the present composition show excellent skin permeation because of their low molecular weight. Accordingly, where the present composition is topically applied to skin, it becomes evident that skin conditions are considerably improved. More still preferably, the improvement in the skin condition by the present composition includes the improvement in wrinkle or skin elasticity, the prevention of skin aging, the prevention of hair loss, the promotion of hair growth, the improvement in skin moisture, the removal of dark spots, the treatment of acne, wound healing and skin regeneration, most preferably, the improvement in wrinkle or skin elasticity, and the prevention of skin aging, wound healing and skin regeneration.

For example, the peptides used as active ingredients in the present composition is able to promote the proliferation of keratinocytes, induce the biosynthesis of procollagen and fibronectin and induce autocrine generation of naturally occurring EGF (one of skin growth substances) to regenerate keratinocyte layer, epidermis and dermis, thereby resulting in the improvements in wrinkle, skin elasticity and skin moisture, the prevention of skin aging, wound healing and skin regeneration.

The present composition may be prepared as a pharmaceutical or cosmetic composition.

According to a preferred embodiment, the composition is a pharmaceutical composition comprising (a) a pharmaceutically effective amount of the peptides of the present invention; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, intraperitoneal, intramuscular, subcutaneous, transdermal or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 µg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferred embodiment, the composition is a cosmetic composition comprising (a) a cosmetically effective amount of the peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isostearly alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention will be summarized as follows:

(i) the EGF-mimicking peptides of the present invention possess identical functions or activities to natural-occurring human EGF;

(ii) the peptides of the present invention are able to promote the generation of autocrine EGF in cells;

(iii) the peptides of the present invention are much higher stability and skin penetration potency than natural-occurring EGF;

(iv) therefore, the composition comprising the peptide exhibits excellent treatment and prevention efficacies on diseases or conditions demanding EGF activities; and (v) the peptide of this invention can be advantageously applied to pharmaceutical compositions, quasi-drugs and cosmetics.

Figure 1:
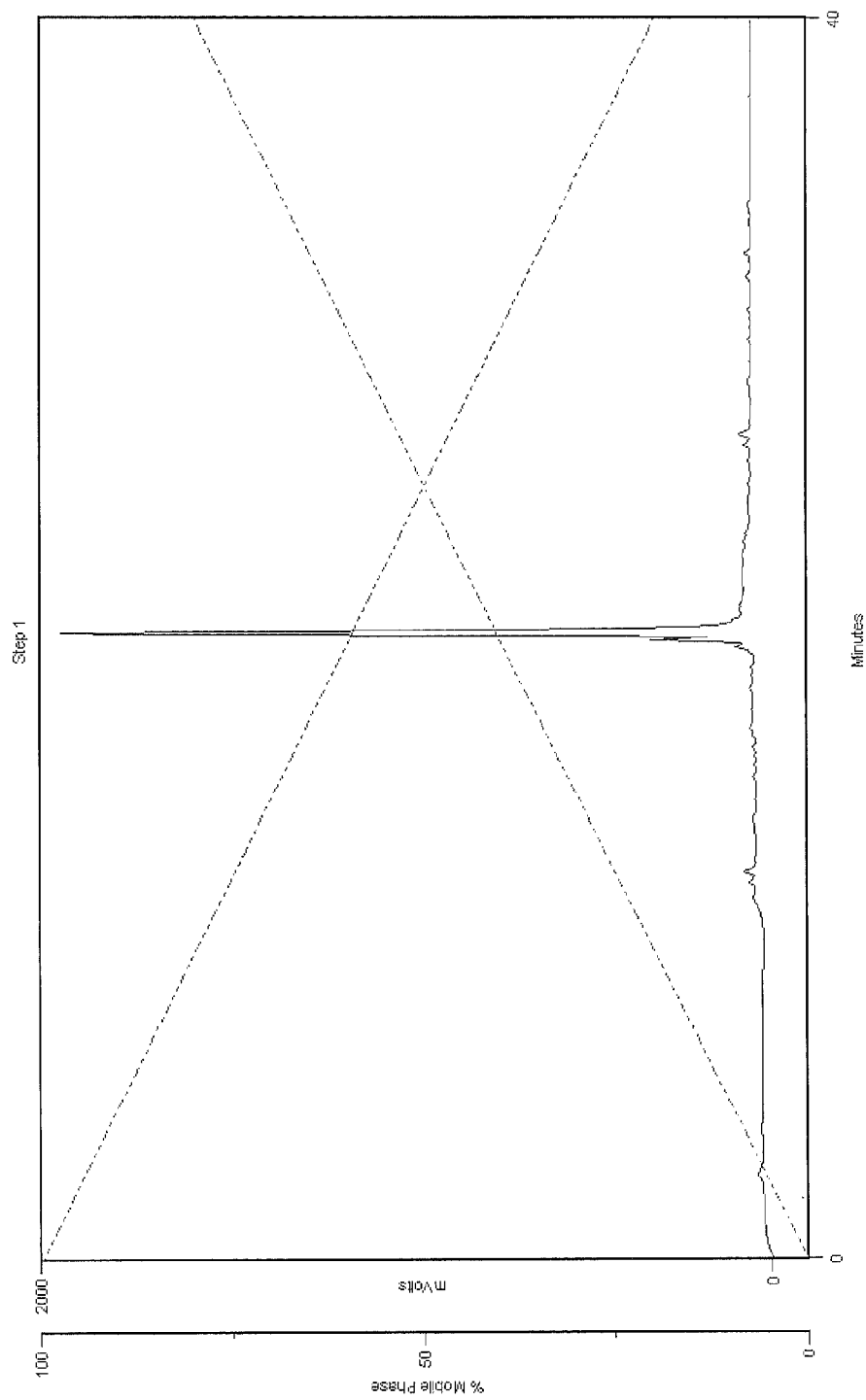
FIG. 1 represents results of HPLC (high performance liquid chromatography) analysis of the tridecapeptide prepared in Example.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of NH2-Cys-Met-Tyr-Ile-Glu-Gly(n)-Arg-Gly-Asp-Gly-OH (SEQ ID NO: 6)

700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Gly-OH Tyr(tBu)-OH (Nova Biochem, USA) and 400 mmole of DIEA (N,N'-diisopropyl ethylamine) were then added to the reactor, after which the mixture was dissolved by agitation and reaction was then undertaken with agitating for 1 hr. After washing, methanol and DIEA (2:1) dissolved in MC were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitated for 10 min at room temperature, followed by removing the solution. After adding the same volume of the deprotection solution, the reaction was undertaken for 10 min and solution was removed, followed by washing sequentially with DMF, MC and DMF to yield Gly-CTL resins. 10 ml of DMF solution was added to a new reactor and then 200 mmole of Fmoc-Asp(tBu)-OH (Nova Biochem, USA), 200 mmole of HoBt and 200 mmole of Bop were added, followed by agitation for solubilization. 400 mmole of DIEA was added to the reactor and agitation was carried out to dissolve all solid contents. The dissolved amino acids solution was introduced into the reactor containing the deprotected resin and reaction was undertaken with agitating for 1 hr at room temperature. Following the removal of the reaction solution, the resultant was agitated three times with DMF solution to remove unreacted residuals. The reacted resin was taken to evaluate extent of reactions by Ninhydrine test. Using the deprotection solution, the deprotection was performed twice in the same manner as described above to yield Asp(tBu)-Gly-CTL resin. After washing with DMF and MC, Ninhydrine test was carried out and the sequential attachments of amino acids were performed as described above. Based on the amino acid sequence designed by the present inventors, Fmoc-Gly, Fmoc-Arg(pbf), Fmoc-Gly(n times), Fmoc-Glu(tBu), Fmoc-Ile, Fmoc-Tyr(tBu), Fmoc-Met and Fmoc-Cys(trt) were sequentially attached to resins. The number of a Gly residue positioned in the middle portion of peptides were varied by carrying out reactions 2-8 time with Fmoc-Gly, generating 7 types of peptidyl resins.

The prepared peptidyl resin was washed three times with DMF, MC and methanol, respectively and dried under nitrogen atmosphere, after which it was vacuum-dried under $P_2O_5$. The dried resins were reacted with 30 ml of a leaving solution [containing 81.5% trifluoroacetic acid (TFA), 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to yield unpurified 7 types of peptides, NH$_2$-Cys-Met-Tyr-Ile-Glu-Gly(n)-Arg-Gly-Asp-Gly-OH (SEQ ID NO: 6). Of them, the peptide consisting of NH$_2$-Cys-Met-Tyr-Ile-Glu-Gly-Gly-Gly-Gly-Arg-Gly-Asp-Gly-OH (SEQ ID NO: 1; hereinafter referred to as tridecapeptide) was produced in the amount of 0.82 g and its molecular weight was measured as 1272.0 using a molecular weight analyzer (Perseptive Pioneer DE-STR ABI, USA).

FIG. 1 represents HPLC analysis results of synthesized peptides. For HPLC analysis, a Gilson pump (Korea Analytical Instruments Co., Ltd., Korea) and $C_{18}$ 4.6×250 mm column were used. The solvent system contained A solvent (0.1% TFA) and B solvent (0.1% MeCN). The synthesized tridecapeptide of this invention was analyzed to have a retention time of about 20 min, addressing that the peptide was obtained with a suitable purity. The following experiments were performed using the tridecapeptide.

Example 2

Evaluation of Stability of Tridecapeptide

Figure 2:
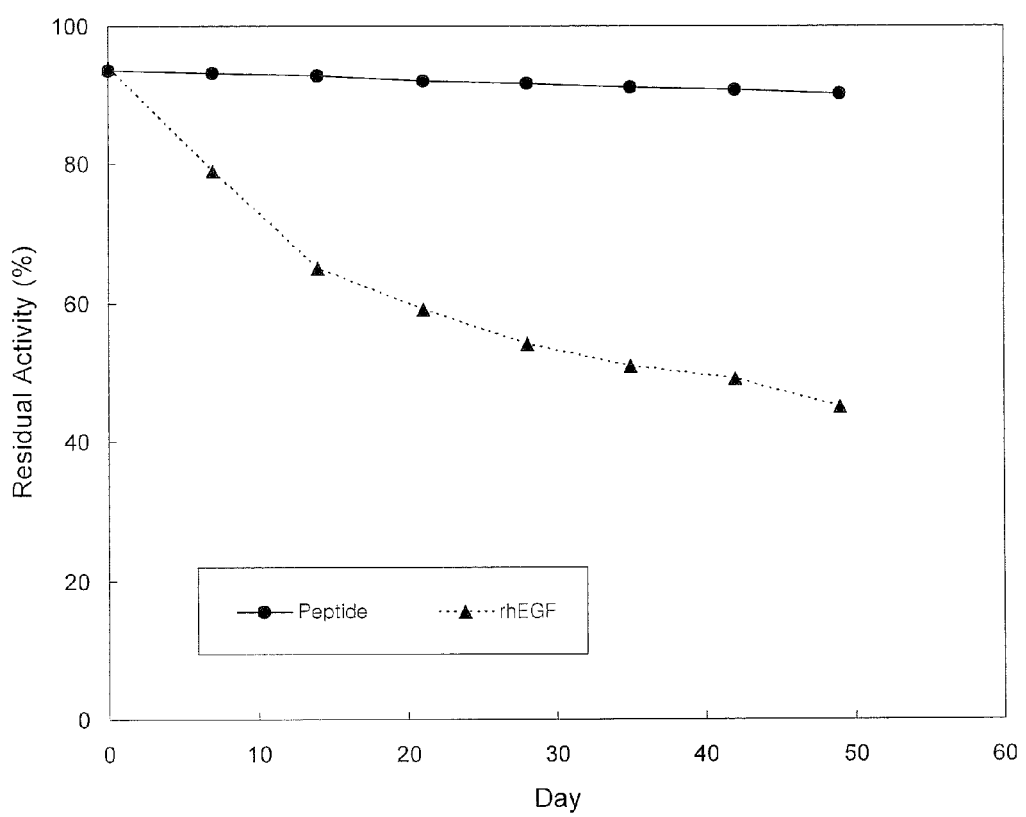
FIG. 2 represents analysis results of stability of the tridecapeptide of this invention. "Peptide" and "rhEGF" indicate the tridecapeptide and recombinant EGF, respectively.

To evaluate stability of the synthesized and purified tridecapeptide of Example 1, the tridecapeptide was dissolved in 50 mM Tris-HCl (pH 8.0) to a concentration of 10 μg/ml. The recombinant EGF protein (Sigma-Aldrich) produced in *E. coli* was prepared as a control in the same buffer to a concentration of 1 μg/ml. The prepared solutions were introduced into glass vials and kept to stand at 37° C. Afterwards, the solutions were taken on days 0, 1, 10, 25, 50, 75 and 100 and subjected to MTT assay (Scudiero, D. A., et al. *Cancer Res.* 48:4827-4833 (1988)) using NIH-3T3 cell (Korean Cell Line Bank) to determine residual activities of the peptide and EGF (FIG. 2). The results were given as relative values to the activity (100%) of sample taken on day 0.

As represented in FIG. 2, the activity of the recombinant EGF protein was sharply decreased with the lapse of time. In contrast, the activity of the present tridecapeptide was shown not to be decreased over time. These results urge us to reason that the EGF peptide of this invention has significantly increased stability compared to the EGF protein having full-length amino acid residues.

Example 3

Preparation of Nano Peptides 50 mg of the tridecapeptide synthesized in Example 1 was dissolved in 500 ml of distilled water. The peptide solution was mixed with 5 g lecithin, 0.3 ml sodium oleate, 50 ml ethanol and a small amount of oils and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics.

Formulation Example 1

Skin Softner

A skin softner comprising tridecapeptide-containing nanosomes prepared in Example 3 was formulated according to the following composition:

TABLE 1

| Ingredients | Content (wt %) |
|---|---|
| Tridecapeptide | 0.001 |
| 1,3-butylene glycol | 6.0 |
| Glycerine | 4.0 |
| PEG 1500 | 1.0 |

TABLE 1-continued

| Ingredients | Content (wt %) |
|---|---|
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream comprising tridecapeptide-containing nanosomes prepared in Example 3 was formulated according to the following composition:

TABLE 2

| Ingredients | Content (wt %) |
|---|---|
| Tridecapeptide | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid comprising tridecapeptide-containing nanosomes prepared in Example 3 was formulated according to the following composition:

TABLE 3

| Ingredients | Content (wt %) |
|---|---|
| Tridecapeptide | 0.002 |
| 1,3-butylene glycol | 4.0 |
| Glycerine | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |

TABLE 3-continued

| Ingredients | Content (wt %) |
|---|---|
| Perfume | Proper amount |
| Distilled water | Residual amount |
| Total | 100 |

Formulation Example 4

Essence

An essence comprising tridecapeptide-containing nanosomes prepared in Example 3 was formulated according to the following composition:

TABLE 4

| Ingredients | Content (wt %) |
|---|---|
| Tridecapeptide | 0.005 |
| Glycerine | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Example 4

Analysis of Effects of Peptides on Growth of HaCaT Keratinocytes

Figure 3:
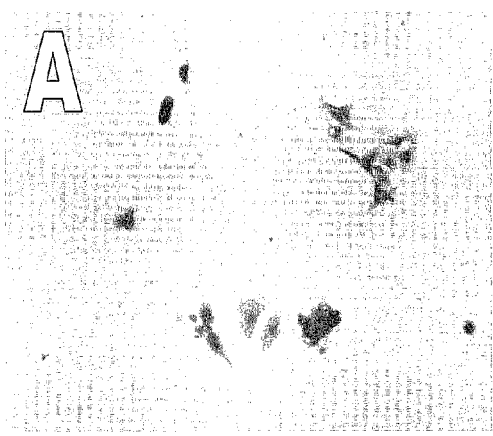
FIG. 3 is a microscope image demonstrating effects of the tridecapeptide to promote the growth of human keratinocytes. Panel A represents non-treated control, and panel B treatment group.
Figure 3:
Figure 4:
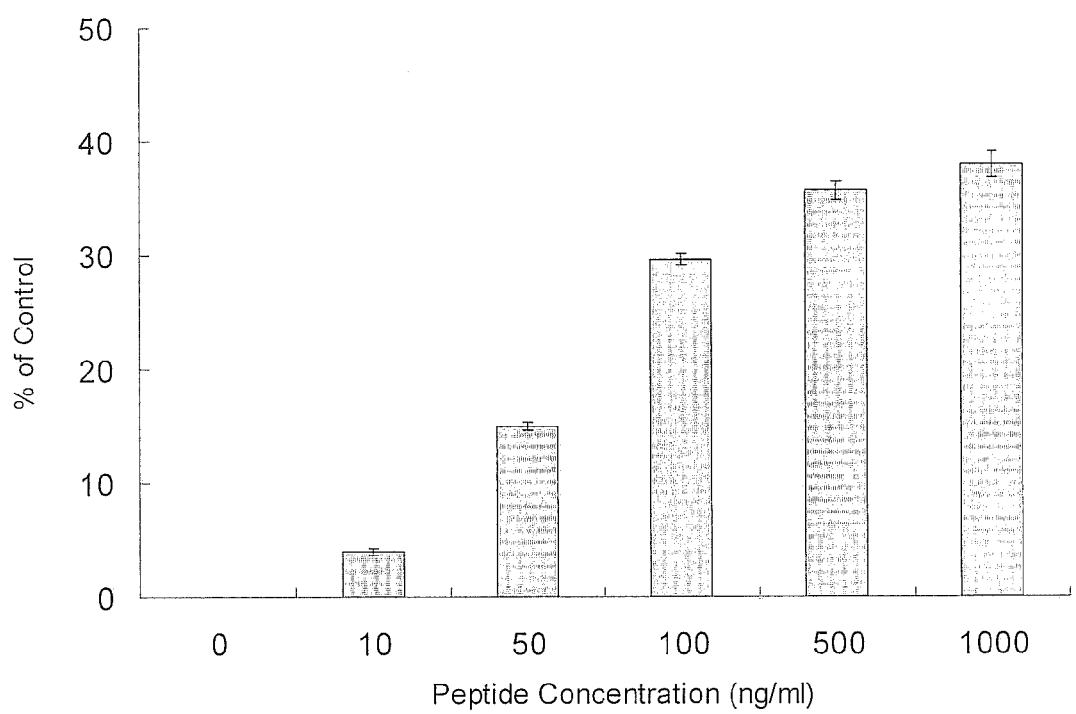
FIG. 4 is a graph demonstrating that the tridecapeptide promotes the growth of human keratinocytes in a dose-dependent manner.
Figure 5:
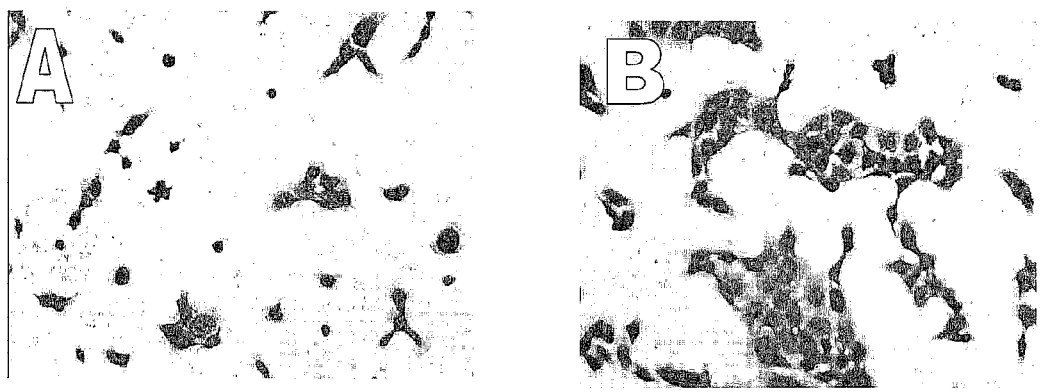
FIG. 5 is a microscope image demonstrating the enhancement of adherency of human keratinocytes by the tridecapeptide.

To analyze effects of peptides of this invention on proliferation of keratinocytes, SRB (Sulforhodamine B) colorimetric assay was carried out using HaCaT kerationcyte according to Rizzino et al method (Rizzino, et al. *Cancer Res.*, 48:4266 (1988)). HaCaT ketatinocytes (The Korean Cell Line Bank) were cultured in 250 ml-flasks containing EMEM (Eagle's minimal essential media, Gibco, U.S.A.) supplemented with 100% FBS (fetal bovine serum). HaCaT ketatinocytes cultured were treated with 0.25% trypsin solution to detach cells from the bottom of culture flasks and centrifuged to collect cell pellets. Cells were resuspended in EMEM not containing FBS, its aliquot ($4\times10^3$) cells was added to each well of 96-well plates and cultured under 7% $CO_2$ for 24 hr at 37° C. After 24-hr culture, the medium was changed with a fresh medium not containing serum and cells were incubated with human EGF or the tri-decapeptide (10 ng/ml or 1,000 ng/ml) dissolved in 10% DMSO for 72 hr under the same conditions as described above. After removing supernatants, cells were washed once using PBS (phosphate buffered saline) and incubated with SRB solution (Sigma-Aldrich). Cells were washed with PBS and observed under a microscope to examine cell viability (FIG. 3). In addition, absorbance at 590 nm was measured to analyze cell proliferation (FIG. 4). Cell adherency to culture dishes was tested using non-treated culture dishes and peptide-pretreated culture dishes. Human keratinocytes were plated on the culture dishes and then incubated for 24 hr, followed by observation under a microscope. As shown in FIG. 5, the number of cells adhered to culture dishes treated with peptides of this invention was observed to be about three-fold greater than that of non-treated culture dishes.

Figure 6:
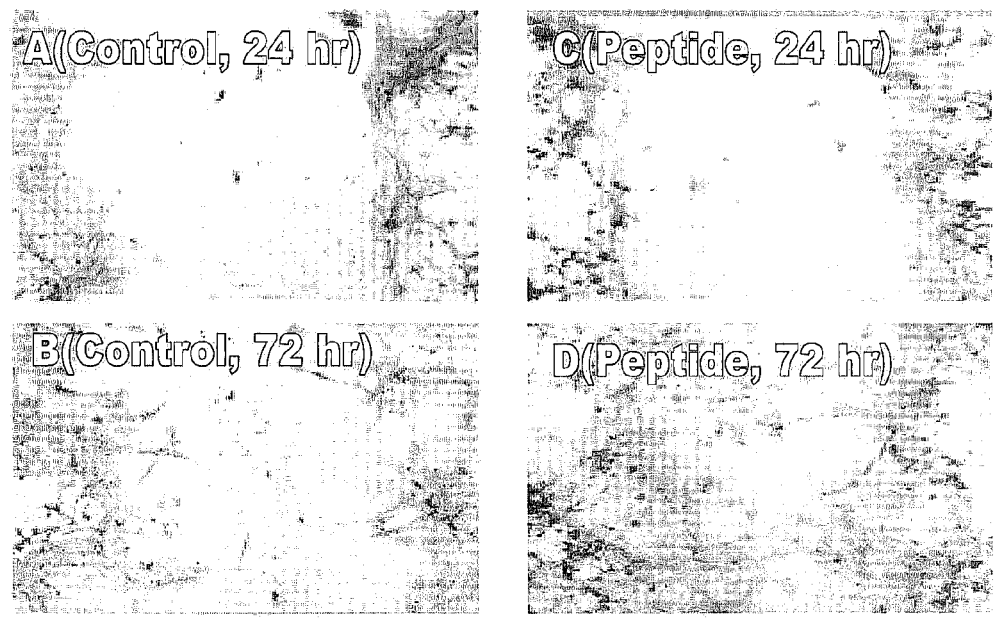
FIG. 6 is a microscope image addressing the increase in motility of NIH 3T3 cells treated with the tridecapeptide.

We analyzed cell motility to further verify cell proliferation potency. NIH3T3 cells were plated on 60 mm-culture dishes and cultured to a suitable fluency. The bottom surface of culture dishes was scratched using pipette and incubated with 1 µg/ml of the present peptides, followed by observing cell motility. In FIG. 6, panels A and B show cell samples non-treated with peptides and panels C and D, cell samples treated with 1 µg/ml peptides. Images of A and C were taken after 1 day-treatment, and those of B and D after 3 day-treatment.

Figure 7:
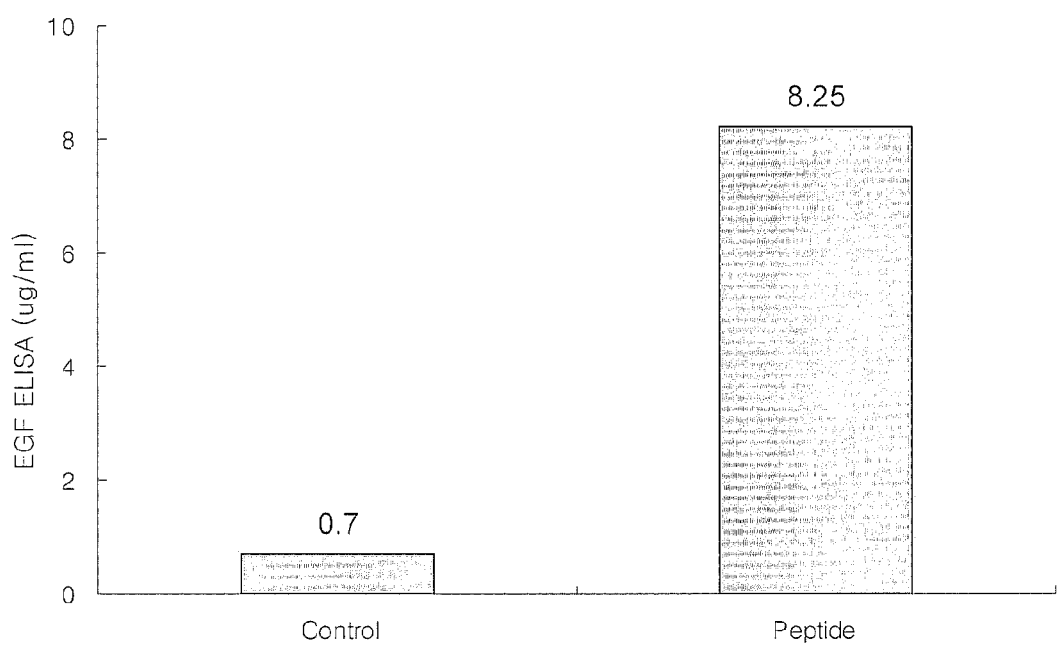
FIG. 7 represents that cells cultured with the tridecapeptide generate autocrine EGF in a higher level.

For examining autocrine effects, HaCat cell lines were incubated for 6 days with the tridecapeptides of this invention (1 µg/ml) and then the level of EGF in culture was measured using the ELISA kit (R&D, USA). We found that the tridecapeptides of this invention have significantly high autocrine effects on EGF (FIG. 7).

Figure 8:
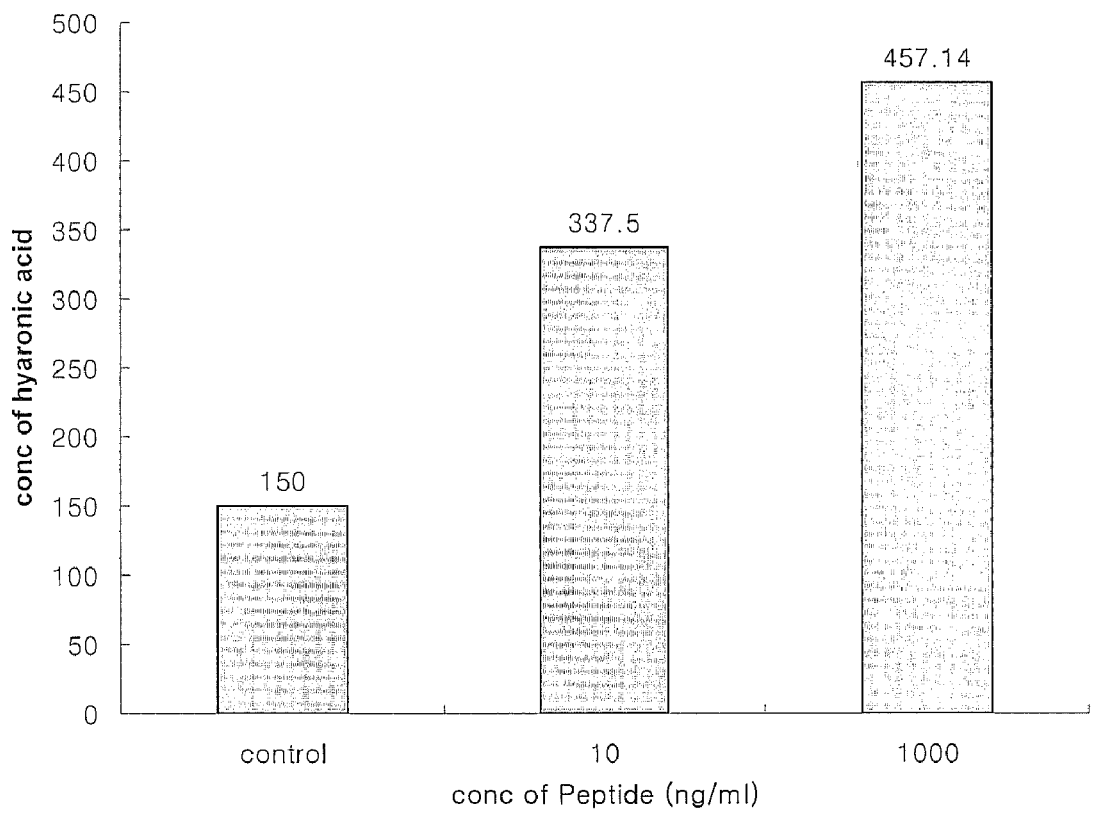
FIG. 8 represents a graph to show the increase in hyaluronic acid levels where culturing cells with the tridecapeptide.

Furthermore, HaCat cell lines were incubated for 72 hr with 5 µmole of the present tridecapeptides and then the level of hyaluronic acid, a marker indicating the improvement in skin wrinkle, was measured using Hyaluronic acid ELISA kit (Echelon Biosciences Inc, USA) (FIG. 8).

As represented in FIGS. 3, 4 and 5, the peptide of this invention exhibits significantly high potency on cell growth, cell viability and adherency. In addition, the peptide of this invention was revealed to promote cell motility. The treatment with the present peptide to HaCaT keratinocytes also induced considerable increase in intracellular EFG level, as shown in FIG. 7. The level of hyaluronic acid was significantly increased by treatment of the present peptide (FIG. 8).

Taken together, it could be appreciated that the peptides of this invention exhibit significantly enhanced effects on the improvement of skin conditions.

Example 5

Analysis of Effects of Peptides on Skin Thickness

For evaluating applicability to cosmetics and in vivo efficacies of the peptides of this invention, the nutrient cream formulated in Formulation Example 2 was applied onto mouse skin.

6-old-week Balb C male mice (Central Lab. Animal, Inc., Korea) were subjected to one-week stabilization and hairs of their back were partially removed using thioglycolic acid-containing cream. Mice were divided into two groups; one group of which was topically administered with the cream comprising tridecapeptide-containing nanosomes and the other group of which was topically administered with cream not containing nanosomes. The application of creams was performed every morning (A.M. 8:30) and evening (P.M. 6:30) for 5 days in the dose of 100 mg. After the application, mice were sacrificed by cervical dislocation and their skin tissues were paraffinized. Paraffinized tissues were sectioned using a microtomb in a thickness of 8 µm and were stained with hematoxyline/eosin, followed by observation under an optical microscope (FIG. 9).

Figure 9:
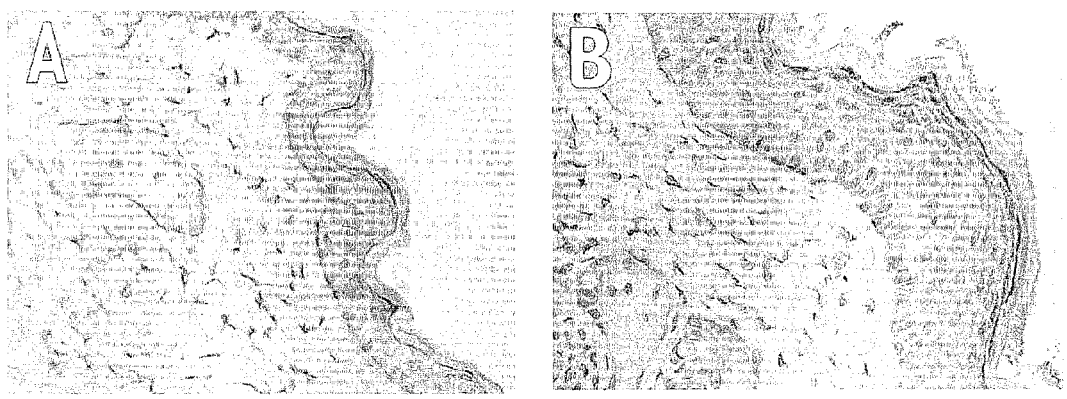
FIG. 9 is a microscope image to show the change in skin thickness of Balb C mice administered with cosmetics containing the tridecapeptide.

As represented in FIG. 9, the nanosome cosmetics comprising the tridecapeptide of this invention allowed to promote the formation and growth of keratinocyte layer and epidermal layer. Accordingly, it could be recognized that cosmetics comprising peptides of this invention exert the improvements in skin wrinkle and elasticity.

The EGF-mimicking peptides of this invention possess activities of naturally occurring human EGF and promote the generation of autocrine EGF in cells. Moreover, the peptides of this invention exhibit superior efficacies and much better stability and skin permeation than natural-occurring bFGF. In these connections, it could understood that the composition comprising the peptides of this invention can exhibit excellent efficacies on the treatment, prevention and improvement of diseases or conditions demanding EGF activities. In addition, the peptides of this invention can be advantageously applied to pharmaceutical compositions, quasi-drugs, cosmetics and cosmeceutics.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A peptide having the activity of epidermal growth factor (EGF), which comprises the amino acid sequence represented by the following formula 1:

(SEQ ID NO: 2)
Cys-Met-Tyr-Ile-Glu-Linker-Arg-Gly-Asp (1), wherein the linker is represented by $Xaa_{(n)}$; Xaa is an amino acid; and n is an integer of 2-10.

2. The peptide according to claim 1, wherein the peptide has at its N-terminal or C-terminal a protection group selected from the group consisting of acetyl group, fluorenyl methoxy carbonyl group, formyl group, palmitoyl group, myristyl group, stearyl group or polyethylene glycol (PEG).

3. The peptide according to claim 1, wherein the Asp residue positioned at the C-terminal of the peptide is additionally linked to an Ala or Gly residue as a protection group.

4. The peptide according to claim 3, wherein the peptide comprises the amino acid sequence represented by the following formula 2:

(SEQ ID NO: 6)
Cys-Met-Tyr-Ile-Glu-Gly(n)-Arg-Gly-Asp-Gly (2)

wherein n is an integer of 2-8.

5. A method for treating an epidermal growth factor-effective disorder or condition, which comprises administering to a subject a composition comprising the peptide of claim 1 having the activity of epidermal growth factor (EGF) as an active ingredient.

6. The method according to claim 5, wherein the composition is a pharmaceutical composition comprising (a) a pharmaceutically effective amount of the peptide of claim 1; and (b) a pharmaceutically acceptable carrier.

7. The method according to claim 5, wherein the composition is a cosmetic composition comprising (a) a cosmetically effective amount of the peptide of claim 1; and (b) a cosmetically acceptable carrier.

8. The method according to claim 5, wherein the composition has efficacies or activities on promotion of cell growth and division, activities of epithelial cells, angiogenesis, neuron regeneration, wound healing, thrombosis treatment, atherosclerosis treatment, biosynthesis of collagen, elastin and laminin, treatment of periodontal diseases or improvement of skin conditions by promoting the generation of natural-occurring EGF.

9. The method according to claim 8, wherein the composition has efficacies on the improvement of skin conditions.

10. The method according to claim 9, wherein the improvement of skin conditions is the improvement in wrinkle or skin elasticity, the promotion of hair growth, the treatment of atopy, the improvement in skin moisture, the removal of dark spots or the treatment of acne.

* * * * *

```
                          SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: EGF-mimicking peptide

<400> SEQUENCE: 1

Cys Met Tyr Ile Glu Gly Gly Gly Gly Arg Gly Asp Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: EGF-mimicking peptide_formula 1
<220> FEATURE:
<221> NAME/KEY: UNSURE
<222> LOCATION: (6)..(6)
<223> OTHER INFORMATION: Xaa is a linker sequence consisting of any
      amino acid of n; n is an integer of 2-10.

<400> SEQUENCE: 2

Cys Met Tyr Ile Glu Xaa Arg Gly Asp
1               5

<210> SEQ ID NO 3
<211> LENGTH: 10
<212> TYPE: PRT
<213> ORGANISM: Artificial Sequence
<220> FEATURE:
<223> OTHER INFORMATION: EGF-mimicking peptide_formula 2
<220> FEATURE:
<221> NAME/KEY: REPEAT
<222> LOCATION: (6)..(6)
<223> OTHER INFORMATION: Xaa is Gly(n) and n is an integer of 2-8

<400> SEQUENCE: 3

Cys Met Tyr Ile Glu Xaa Arg Gly Asp Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Artificial Sequence

<400> SEQUENCE: 4

Cys Met Tyr Ile Glu
1               5

<210> SEQ ID NO 5
<211> LENGTH: 9
```

-continued

```
<212> TYPE: PRT
<213> ORGANISM: Artificial Sequence
<220> FEATURE:
<223> OTHER INFORMATION: EGF-mimicking peptide
<220> FEATURE:
<221> NAME/KEY: UNSURE
<222> LOCATION: (4)..(4)
<223> OTHER INFORMATION: Xaa is a linker sequence consisting of any
      amino acid of n; n is an integer of 2-10.

<400> SEQUENCE: 5

Arg Gly Asp Xaa Cys Met Tyr Ile Glu
1               5

<210> SEQ ID NO 6
<211> LENGTH: 10
<212> TYPE: PRT
<213> ORGANISM: Artificial Sequence
<220> FEATURE:
<223> OTHER INFORMATION: EGF-mimicking peptide
<220> FEATURE:
<221> NAME/KEY: UNSURE
<222> LOCATION: (6)..(6)
<223> OTHER INFORMATION: Xaa is a linker sequence consisting of any
      amino acid of n; n is an integer of 2-8.

<400> SEQUENCE: 6

Cys Met Tyr Ile Glu Xaa Arg Gly Asp Gly
1               5                   10
```